(12) United States Patent
Baynham

(10) Patent No.: US 10,327,909 B2
(45) Date of Patent: Jun. 25, 2019

(54) CERVICAL CAGE

(71) Applicant: Atlas Spine, Inc., Jupiter, FL (US)

(72) Inventor: Matthew G. Baynham, Jupiter, FL (US)

(73) Assignee: Atlas Spine, Inc., Jupiter, FL (US)

( * ) Notice: Subject to any disclaimer, the term of this patent is extended or adjusted under 35 U.S.C. 154(b) by 9 days.

(21) Appl. No.: 15/609,789

(22) Filed: May 31, 2017

(65) Prior Publication Data
US 2018/0344475 A1 Dec. 6, 2018

(51) Int. Cl.
*A61F 2/44* (2006.01)
*A61B 17/70* (2006.01)
*A61F 2/30* (2006.01)

(52) U.S. Cl.
CPC ........ *A61F 2/4425* (2013.01); *A61B 17/7059* (2013.01); *A61F 2/4455* (2013.01); *A61F 2002/30326* (2013.01); *A61F 2002/30405* (2013.01); *A61F 2002/30537* (2013.01)

(58) Field of Classification Search
CPC ....................... A61F 2/44–2/447; A61F 2/4611
See application file for complete search history.

(56) References Cited

U.S. PATENT DOCUMENTS

| | | | | |
|---|---|---|---|---|
| 5,554,191 | A * | 9/1996 | Lahille | A61B 17/1671 411/55 |
| 8,491,657 | B2 * | 7/2013 | Attia | A61F 2/447 623/17.16 |
| 8,663,329 | B2 * | 3/2014 | Ernst | A61F 2/4465 623/17.15 |
| 8,778,025 | B2 * | 7/2014 | Ragab | A61F 2/447 623/17.11 |
| 8,845,728 | B1 * | 9/2014 | Abdou | A61F 2/4455 623/17.11 |
| 9,445,919 | B2 * | 9/2016 | Palmatier | A61F 2/447 |
| 9,486,328 | B2 * | 11/2016 | Jimenez | A61F 2/447 |
| 9,713,536 | B2 * | 7/2017 | Foley | A61F 2/4455 |
| 9,848,993 | B2 * | 12/2017 | Moskowitz | A61B 17/0642 |
| 9,848,996 | B2 * | 12/2017 | Faulhaber | A61F 2/447 |
| 9,901,459 | B2 * | 2/2018 | Faulhaber | A61F 2/4455 |
| 9,907,670 | B2 * | 3/2018 | DeRidder | A61F 2/4455 |
| 10,004,608 | B2 * | 6/2018 | Carnes | A61F 2/447 |
| 10,016,225 | B2 * | 7/2018 | Moskowitz | A61B 17/0642 |
| 2010/0292796 | A1 * | 11/2010 | Greenhalgh | A61B 17/8858 623/17.11 |
| 2011/0093074 | A1 * | 4/2011 | Glerum | A61F 2/447 623/17.16 |
| 2011/0144755 | A1 * | 6/2011 | Baynham | A61F 2/447 623/17.16 |
| 2014/0257486 | A1 * | 9/2014 | Alheidt | A61F 2/447 623/17.15 |
| 2014/0288653 | A1 * | 9/2014 | Chen | A61F 2/447 623/17.16 |

(Continued)

*Primary Examiner* — Nicholas J Plionis
*Assistant Examiner* — Steven J Cotroneo
(74) *Attorney, Agent, or Firm* — McHale & Slavin, P.A.

(57) ABSTRACT

A cervical plate formed from an expandable clip that is drawn toward a plate by use of a draw screw coupled to a draw bar. The draw bar is placed in an aperture having engagement with an angular surface that operates in conjunction with a proximal and distal end of the clip, which engages a tab to cause expansion when the draw screw engages the draw bar across a plate.

7 Claims, 5 Drawing Sheets

(56) References Cited

U.S. PATENT DOCUMENTS

| | | | | |
|---|---|---|---|---|
| 2015/0342748 | A1* | 12/2015 | Baynham | A61F 2/447 623/17.15 |
| 2016/0166396 | A1* | 6/2016 | McClintock | A61F 2/30771 623/17.16 |
| 2016/0354212 | A1* | 12/2016 | Baynham | A61F 2/447 |
| 2016/0367377 | A1* | 12/2016 | Faulhaber | A61F 2/447 |

* cited by examiner

CERVICAL CAGE

FIELD OF THE INVENTION

This invention relates to the field of orthopedic surgery and, more particularly, to implants to be placed between vertebrae in the spine.

BACKGROUND OF THE INVENTION

Spinal stabilization is known to alleviate chronic back pain caused by displaced disk material or excessive movement of individual vertebrae. Conventional stabilization techniques include fusing two or more vertebrae together to immobilize the area of excessive movement. In one technique, vertebral disk material which separates the vertebrae is removed, and bone graft material is inserted in the space for interbody fusion. In addition to, or in place of, the bone graft material, a spinal implant may be inserted in the intervertebral space.

The conventional surgical approach for stabilization has been posteriorly for ease of access to the spine and to avoid interfering with internal organs and tissue. Usually, the implant site is prepared to maintain natural lordosis and to accept a certain sized implant within certain pressure limits. This requires considerable time and skill by the surgeon.

SUMMARY OF THE INVENTION

Disclosed is an implant forming an expandable cervical cage having a clip engaged by a draw bar that is drawn to expand the cage to a preferred height and increase the angle between a top and a bottom surface to restore the natural curvature of the spine. The clip includes a plate that holds the expandable cervical cage in position with bone screws.

Accordingly, it is an objective of the instant invention to teach a posterior surgical approach for placement of an intervertebral spacer implant for interbody fusion, allowing the implant to be inserted through a small incision and increased in size in situ.

It is yet another objective of the instant invention to teach an implant facilitating spinal alignment by use of a clip having an angular drive surface shaped to expand a top and bottom surface of the clip to achieve spacing.

It is yet another objective of the instant invention to teach an implant facilitating spinal alignment by use of a clip having an angular drive surface shaped to expand a top and bottom surface of the clip to achieve angular positioning.

Other objectives and advantages of this invention will become apparent from the following description taken in conjunction with any accompanying drawings; wherein are set forth, by way of illustration and example, certain embodiments of this invention. Any drawings contained herein constitute a part of this specification and include exemplary embodiments of the present invention and illustrate various objects and features thereof.

DETAILED DESCRIPTION OF THE INVENTION

Figure 1:
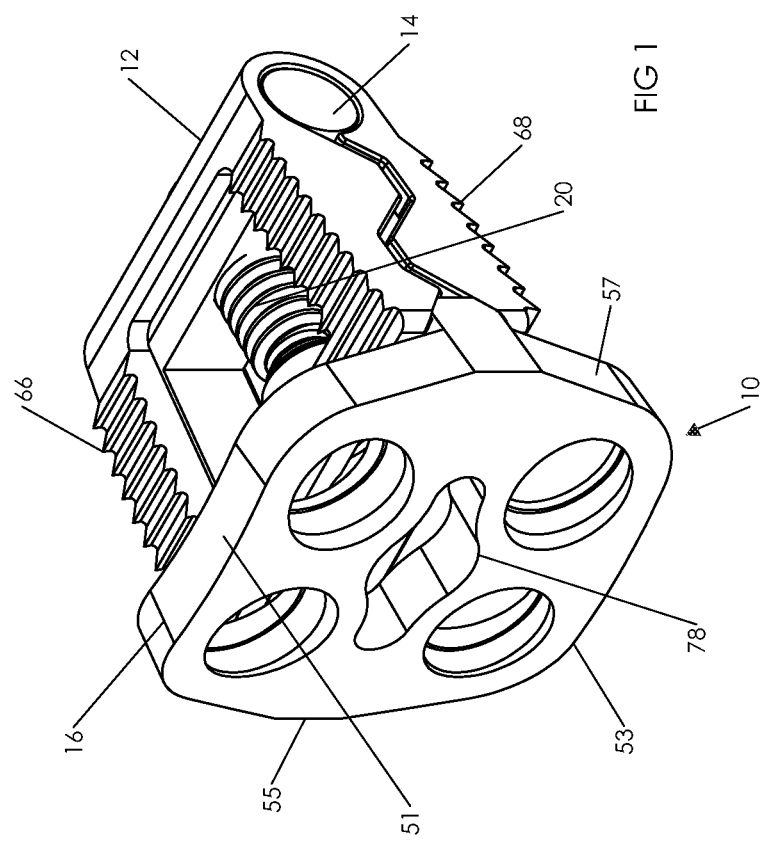
FIG. 1 is an perspective view of the spinal implant.
Figure 2:
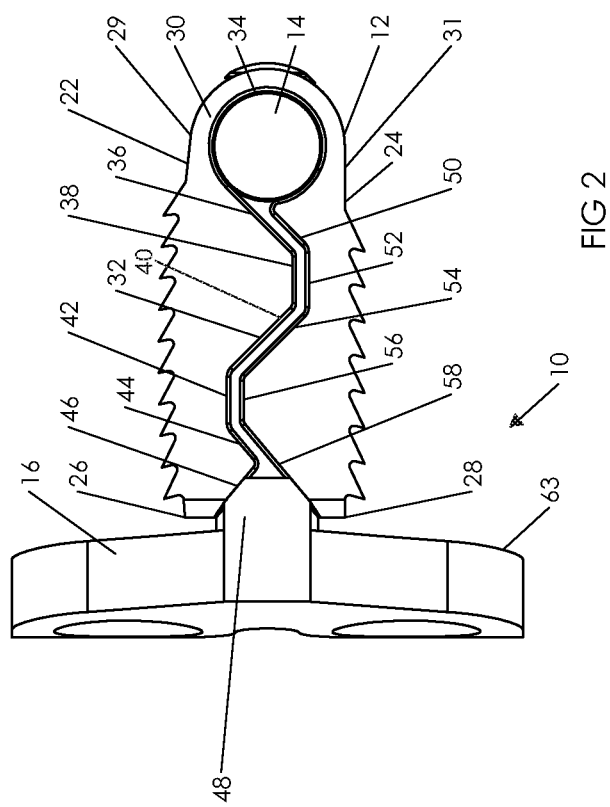
FIG. 2 is a side view of the spinal implant.

The cervical cage implant 10 is inserted in the intervertebral space to replace damaged, missing or excised disk material. In particular the cervical cage 10 is placed between adjacent vertebrae which are forced apart to a desired spacing.

Referring now in general to the figures, depicted is the cervical cage 10 of the instant invention which consists of an expandable clip 12, a draw bar 14, a plate 16, and a draw screw 20. The expandable clip 12 is formed from a single piece element 30 shaped to define an upper member 22 and a lower member 24 having a proximal end 26 and distal end 28. The expandable clip 12 can be made of conventional materials commonly used in surgical implants, such as stainless steel and its many different alloys, titanium, or any other material with the requisite strength and biologically inert properties. Polymeric materials with adequate strength and biological properties may also be used in the construction of the expandable clip 12, draw bar 14, plate 16 and draw screw 20. The proximal end 26 and distal end 28 are juxtapositioned, wherein the element 30 wraps around the draw bar 14, forming an aperture 34 which operates in conjunction with the draw bar 14 as a pivot point between the upper member 22 and the lower member 24. The upper member 22 includes an upper inner surface 32 that extends from the aperture 34 that encompasses the draw bar 14 having a first angular surface 36 extending from the top of the aperture 34 to a second inner surface 38 which is substantially parallel to the top surface 29 of the upper member 22. A third inner surface 40 extends from the second surface 38 at an angular slope toward the top surface 29, adjoining a fourth inner surface 42 which is substantially parallel to the upper member 22 top surface 29 and second inner surface 38. A fifth inner surface 44 extends from the fourth inner surface 42 in a downward angle to form a length about one half of the length of the first angular surface 36. A sixth inner surface 46 is angular upward and engages an expansion tab 48 on the plate 16.

Similarly, the lower member 24 has a first inner surface 50 which is constructed and arranged to abut first angular surface 36, wherein movement of the draw bar 14 towards the plate 16 results in the raising of the upper member 22 as it slides along the first inner surface 50 and the draw bar 14 as it engages the first angular surface 36 of the upper member 22 during adjustment, when the draw screw is rotated in respect to the draw bar 14. The second inner surface 38 of the upper member 22 corresponds with a second inner surface 52 of the lower member 24, which maintains the upper surface 29 and the lower surface 31 in a uniform position as the expandable clip 12 is raised through draw bar 14 movement. Lower member 24 includes a third inner surface 54 which operates in conjunction with the third inner surface 40 of the upper member 22 so as to maintain the spatial distance that is uniform between the upper member 22 and lower member 24 as the portions expand during draw bar 14 rotation. The fourth inner surface 56 of the lower member 24 operates in conjunction with the inner surface 42 of the upper member 22 to maintain the upper member 22 and lower member 24 in a uniform position during distraction. The fifth inner surface 58 of the lower member 24 operates with the plate 16 and expansion tab 48 so as to cause a uniform distraction and expansion of the expandable clip upper member 22 and lower member 24 as the draw bar 14 is drawn towards the plate 16, causing the sixth inner surface 46 and fifth inner surface 58 to expand in a uniform expansion while draw bar 14 is drawn towards the plate 16.

Figure 3:
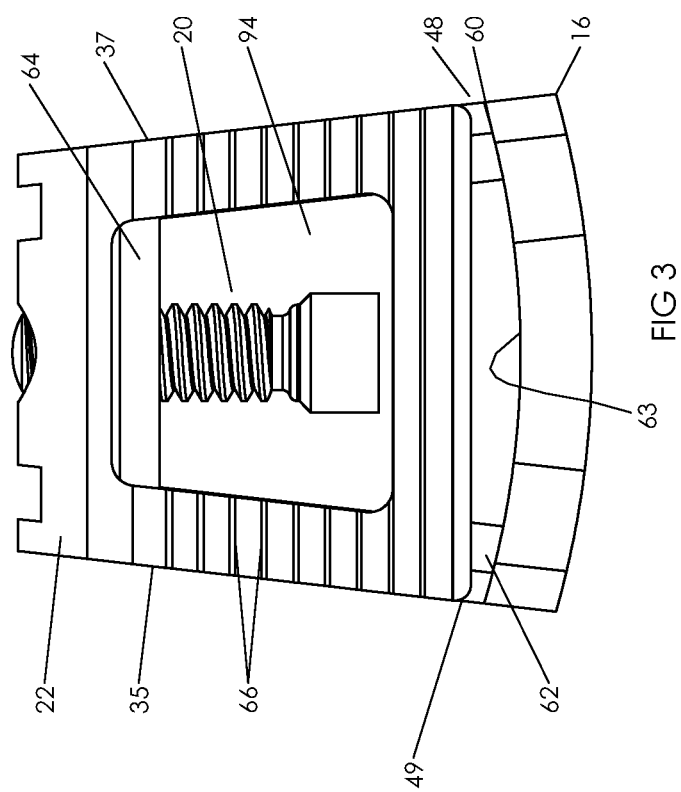
FIG. 3 is a top view thereof.

As shown in the FIG. 3, the plate 16 includes a frame 60 that extends from the back 63 of the plate 16 with struts 62 formed with a cross-strut 64 for engagement of the draw screw 20. The shank of the draw screw 20 is passed through the cross-strut 64 for engaging of the draw bar 14. The upper member 22 includes ridges or stippled teeth 66 to engage bone material in a conventional manner to prevent disengagement of the expandable clip from bone upon installation. Stippled teeth 68 are located on the lower member 24, operating in a similar manner as the upper portion stippled teeth 66, preferably including a directional slope to the teeth to allow ease of insertion of the implant and prevent disengagement from the bone. Each member includes a centrally disposed aperture 94 for receipt of bone growth material.

Figure 4:
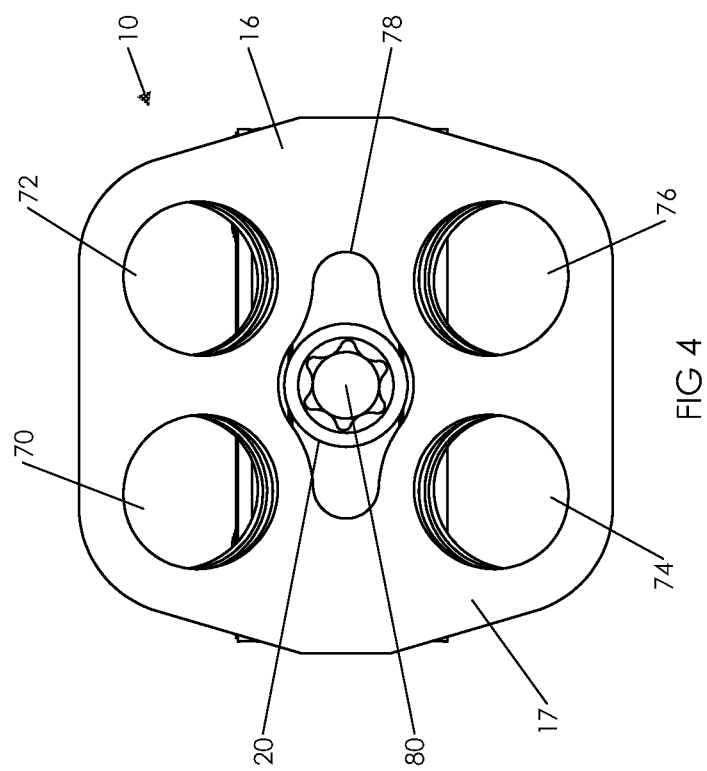
FIG. 4 is a front view thereof.

FIG. 4 depicts a front view of the cervical cage 10 having threaded apertures 70, 72, 74 and 76, which secure the cervical cage to bone by use of bone screws, not shown, placed through each of the apertures. The center aperture 78 allows accessibility to the end 80 of the draw screw 20, so as to allow expansion of the expandable clip 12 by rotation of the screw 20. It is noted that the apertures 70, 72, 74 and 76 are angled in a conventional manner so as to provide better purchase into the bone, yet allow clearance for the proximal end 26 and distal end 28 of the expandable clip 12 for adjustment.

Figure 5:
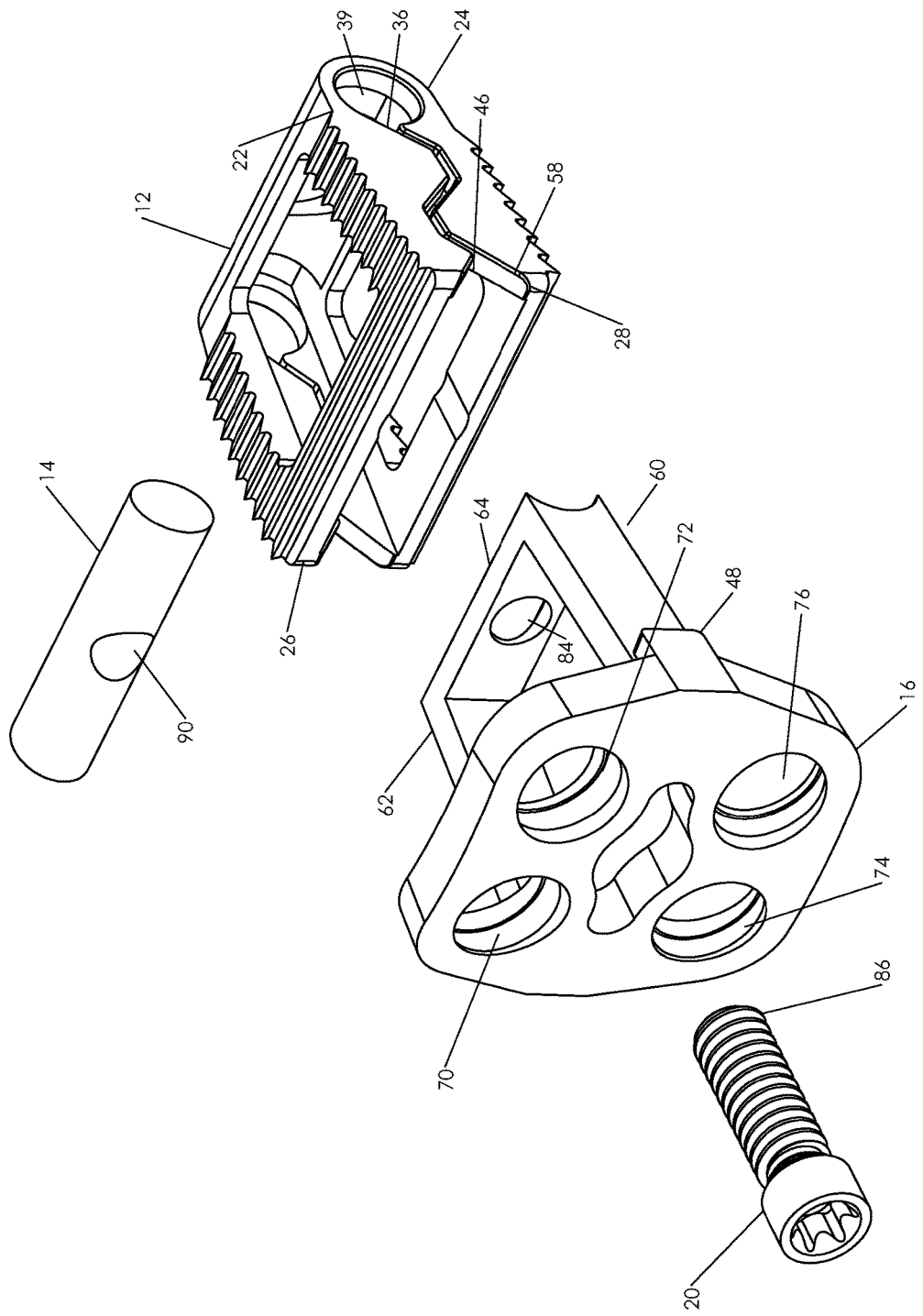
FIG. 5 is an exploded view thereof.

Referring now to FIG. 5, shown is the expandable clip 12 with the draw screw 20 shown in an exploded view apart from the plate 16, with support struts 62 and connected cross-strut 64. An aperture 84 is positioned in the cross-strut 64 for insertion placement of the distal end 86 of the draw screw 20 for engaging a threaded receptacle 90 in the draw bar 14. The plate 16 includes an expansion tab 48 located on the back surface 63, which operates to spread the upper member 22 and lower member 24, and the fifth lower inner surface 58 and sixth lower inner surface 46 when the draw screw 20 is drawn. As the clip 12 is drawn towards the back 63 of the plate 16, surfaces 46 and 58 engage tab 48, causing an expansion as tab requires the proximal end 26 and distal end 28 to expand at the same time the draw bar 14 is causing the first surface 36 to rise over the draw bar, allowing for an angular expansion of the upper member. The cervical implant may be used unilaterally or bilaterally.

The expandable clip 12 has an upper member 22 with a substantially planar top surface 29 and an angular shaped bottom surface 36 with a proximal end 26 with opposing side surfaces 35, 37 extending to a hinged end 30 conjoined with a lower member 24 having a substantially planar lower surface 31 and an angular shaped first inner surface 50 constructed and arranged to interface with the angular shaped bottom surface 36 of the upper member 22, the lower member 24 having a distal end 28 juxtapositioned to the proximal end 26, the hinged end 30 forming an aperture 39 extending between the opposing side surfaces 35, 37; a draw bar 14 insertable into the aperture 39 of the hinged end 30 having a centrally disposed threaded receptacle 90 for receipt of a draw screw 20; a plate 16 has a top wall 51, a bottom wall 53, and side walls 55, 57 with a front surface 17 and a back surface 63 defining a width therebetween, the plate 16 having a plurality of bone screw receptacles 70, 72, 74, 76 and a strut means 60, 62, 64 for maintaining the draw screw 20 for engaging the draw bar 14, the plate 16 including first and second expansion tabs 48, 49; the draw screw 20 engages the plate 16 to pull the draw bar 14 toward the plate 16, the proximal 26 and distal end 28 of the expandable clip 12 engaging the tabs 48, 49 to create an expansion distance between the upper 22 and lower member 24 with the draw bar 14 engaging the angular shaped inner surface 36, providing uniform expansion distance.

It is to be understood that while a certain form of the invention is illustrated, it is not to be limited to the specific form or arrangement herein described and shown. It will be apparent to those skilled in the art that various changes may be made without departing from the scope of the invention, and the invention is not to be considered limited to what is shown and described in the specification and any drawings/figures included herein.

One skilled in the art will readily appreciate that the present invention is well adapted to carry out the objectives and obtain the ends and advantages mentioned, as well as those inherent therein. The embodiments, methods, procedures and techniques described herein are presently representative of the preferred embodiments, are intended to be exemplary, and are not intended as limitations on the scope. Changes therein and other uses will occur to those skilled in the art which are encompassed within the spirit of the invention and are defined by the scope of the appended claims. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A cervical implant comprising:
   an expandable clip formed from a single piece element defined by an upper member having a top surface and an angular shaped bottom surface with a proximal end with opposing side surfaces extending to a hinged end conjoined with a lower member having a lower surface and an angular shaped inner surface constructed and arranged to interface with said angular shaped bottom surface of said upper member, said lower member having a distal end juxtapositioned to said proximal end, said hinged end forming an aperture extending between said opposing side surfaces;
   a draw bar insertable into said aperture of said hinged end having a centrally disposed threaded receptacle for receipt of a draw screw;
   a plate having a top wall, a bottom wall, and two side walls with a front surface and a back surface defining a width therebetween for support of a frame element, said plate having a plurality of bone screw receptacles and a strut for maintaining a draw screw for engaging said draw bar, said plate including first and second expansion tabs;
   said draw screw engages said plate to pull said draw bar toward said plate, said proximal and distal end of said expandable clip engaging said tabs to create an expansion distance between said upper member proximal end and said lower member distal end while maintaining a fixed distance along said hinged end.

2. The cervical implant according to claim 1 wherein said upper surface of said top member and said outer surface of said bottom member have stippled teeth.

3. The cervical implant according to claim 1 wherein angular shaped inner surface includes a surface for engaging said draw bar for an angular predefined displacement.

4. The cervical implant according to claim 1 wherein said angular shaped inner surface includes a tapered proximal end and a tapered distal end to facilitate tab insertion for expansion between said members.

5. The cervical implant according to claim 1 wherein upper and lower members include a centrally disposed aperture for receipt of bone growth material.

6. The cervical implant according to claim 1 wherein said implant may be used unilaterally or bilaterally.

7. The cervical implant according to claim 1 wherein said inner surface of said upper member having an angular shaped bottom surface with a first and second angled surface interfacing with said inner surface of said lower member having a first and second angled, wherein said angled surfaces of said upper member and said lower member are slidably engaged.

\* \* \* \* \*